United States Patent
Rice et al.

(10) Patent No.: US 7,980,963 B2
(45) Date of Patent: *Jul. 19, 2011

(54) METAL WOOD CLUB WITH IMPROVED HITTING FACE

(75) Inventors: Scott A. Rice, San Diego, CA (US); Nicholas M. Nardacci, Bristol, RI (US)

(73) Assignee: Acushnet Company, Fairhaven, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/694,555

(22) Filed: Jan. 27, 2010

(65) Prior Publication Data

US 2010/0190571 A1  Jul. 29, 2010

Related U.S. Application Data

(63) Continuation of application No. 11/221,221, filed on Sep. 7, 2005, now Pat. No. 7,704,162, which is a continuation-in-part of application No. 10/911,422, filed on Aug. 4, 2004, now Pat. No. 7,261,643, and a continuation-in-part of application No. 10/911,341, filed on Aug. 4, 2004, now Pat. No. 7,207,898, which is a continuation-in-part of application No. 10/428,061, filed on May 1, 2003, now Pat. No. 7,029,403, which is a continuation-in-part of application No. 09/551,771, filed on Apr. 18, 2000, now Pat. No. 6,605,007.

(51) Int. Cl.
    *A63B 53/04* (2006.01)
(52) U.S. Cl. ........ 473/329; 473/342; 473/345; 473/346; 473/349

(58) Field of Classification Search .......... 473/324–350, 473/287–292
See application file for complete search history.

(56) References Cited

U.S. PATENT DOCUMENTS

| | | | |
|---|---|---|---|
| 1,318,325 A | 10/1919 | Klin |
| 1,319,233 A | 10/1919 | Mattern |
| 1,467,435 A | 9/1923 | Kinnear |
| 1,525,352 A | 2/1925 | Aitken |

(Continued)

FOREIGN PATENT DOCUMENTS

CN          1114911        1/1996

(Continued)

OTHER PUBLICATIONS

Golf Digest, Sep. 1982, p. 25.

(Continued)

*Primary Examiner* — Sebastiano Passaniti
(74) *Attorney, Agent, or Firm* — Randy K. Chang

(57) ABSTRACT

A hitting face of a golf club head having a location of longest characteristic time shifted away from the geometric center of the hitting face. In one embodiment, the hitting face is made from multiple materials. In another embodiment, the hitting face as a central zone that is thicker than the surrounding material. In another embodiment, a dense insert is attached directly or indirectly to a plate-like face insert at or near the geometric center of the insert. In another embodiment, the central zone of the hitting face is reinforced with ribs. In another embodiment, the central zone is elliptical with varying thickness. In this embodiment, the central zone minor axis is thinner than the major axis. The central zone is positioned within the hitting face such that the minor axis is oriented from the low heel region to the high toe region.

14 Claims, 7 Drawing Sheets

U.S. PATENT DOCUMENTS

| | | | |
|---|---|---|---|
| 1,543,691 A | 6/1925 | Beat | |
| 1,582,836 A | 4/1926 | Link | |
| 1,589,363 A | 6/1926 | Butchart | |
| 1,595,589 A | 8/1926 | Tyler | |
| 1,605,551 A | 11/1926 | Mattern | |
| 1,699,874 A | 1/1929 | Buhrke | |
| 1,704,119 A | 3/1929 | Buhrke | |
| 1,704,165 A | 3/1929 | Buhrke | |
| 1,720,867 A | 7/1929 | Webster et al. | |
| 2,034,936 A | 3/1936 | Barnhart | |
| 2,087,685 A | 7/1937 | Hackney | |
| 3,567,228 A | 3/1971 | Lynn | |
| 3,571,900 A | 3/1971 | Hardesty | |
| 3,625,518 A | 12/1971 | Solheim | |
| 3,659,855 A | 5/1972 | Hardesty | |
| 3,863,932 A | 2/1975 | Lezatte | |
| 3,985,363 A | 10/1976 | Jepson et al. | |
| 4,023,802 A | 5/1977 | Jepson et al. | |
| 4,193,601 A | 3/1980 | Reid, Jr. et al. | |
| 4,213,613 A | 7/1980 | Nygren | |
| 4,214,754 A | 7/1980 | Zebelean | |
| D267,965 S | 2/1983 | Kobayashi | |
| 4,429,879 A | 2/1984 | Schmidt | |
| 4,432,549 A | 2/1984 | Zebelean | |
| 4,449,707 A | 5/1984 | Hayashi et al. | |
| 4,451,041 A | 5/1984 | Hayashi et al. | |
| 4,451,042 A | 5/1984 | Hayashi et al. | |
| 4,465,221 A | 8/1984 | Schmidt | |
| 4,471,961 A | 9/1984 | Masghati et al. | |
| 4,489,945 A | 12/1984 | Kobayashi | |
| 4,511,145 A | 4/1985 | Schmidt | |
| 4,762,324 A | 8/1988 | Anderson | |
| 4,792,140 A | 12/1988 | Yamaguchi et al. | |
| 4,826,172 A | 5/1989 | Antonious | |
| 4,842,243 A | 6/1989 | Butler | |
| 4,913,438 A | 4/1990 | Anderson | |
| 4,915,385 A | 4/1990 | Anderson | |
| 4,915,386 A | 4/1990 | Antonious | |
| 4,919,430 A | 4/1990 | Antonious | |
| 4,919,431 A | 4/1990 | Antonious | |
| 4,921,252 A | 5/1990 | Antonious | |
| 4,928,965 A | 5/1990 | Yamaguchi et al. | |
| 4,930,781 A | 6/1990 | Allen | |
| 4,932,658 A | 6/1990 | Antonious | |
| 4,955,610 A | 9/1990 | Creighton et al. | |
| D312,858 S | 12/1990 | Anderson et al. | |
| 5,000,454 A | 3/1991 | Soda | |
| 5,024,437 A | 6/1991 | Anderson | |
| 5,028,049 A | 7/1991 | McKeighen | |
| 5,046,733 A | 9/1991 | Antonious | |
| 5,056,705 A | 10/1991 | Wakita et al. | |
| 5,060,951 A | 10/1991 | Allen | |
| 5,067,715 A | 11/1991 | Schmidt et al. | |
| 5,090,702 A | 2/1992 | Viste | |
| 5,094,383 A | 3/1992 | Anderson et al. | |
| 5,106,094 A | 4/1992 | Desbiolles et al. | |
| 5,141,230 A | 8/1992 | Antonious | |
| 5,163,682 A | 11/1992 | Schmidt et al. | |
| 5,180,166 A | 1/1993 | Schmidt et al. | |
| 5,183,255 A | 2/1993 | Antonious | |
| 5,213,328 A | 5/1993 | Long et al. | |
| 5,221,087 A | 6/1993 | Fenton et al. | |
| 5,240,252 A | 8/1993 | Schmidt et al. | |
| 5,242,167 A | 9/1993 | Antonious | |
| 5,255,918 A | 10/1993 | Anderson et al. | |
| 5,261,663 A | 11/1993 | Anderson | |
| 5,261,664 A | 11/1993 | Anderson | |
| 5,271,621 A | 12/1993 | Lo | |
| 5,292,129 A | 3/1994 | Long et al. | |
| 5,295,689 A | 3/1994 | Lundberg | |
| 5,301,945 A | 4/1994 | Schmidt et al. | |
| 5,318,300 A | 6/1994 | Schmidt et al. | |
| 5,328,184 A | 7/1994 | Antonious | |
| 5,344,140 A | 9/1994 | Anderson | |
| 5,346,218 A | 9/1994 | Wyte | |
| 5,351,958 A | 10/1994 | Helmstetter | |
| 5,358,249 A | 10/1994 | Mendralla | |
| 5,362,047 A | 11/1994 | Shaw et al. | |
| 5,362,055 A | 11/1994 | Rennie | |
| 5,366,223 A | 11/1994 | Werner et al. | |
| 5,380,010 A | 1/1995 | Werner et al. | |
| 5,390,924 A | 2/1995 | Antonious | |
| 5,395,113 A | 3/1995 | Antonious | |
| 5,397,126 A | 3/1995 | Allen | |
| 5,401,021 A | 3/1995 | Allen | |
| 5,405,136 A | 4/1995 | Hardman | |
| 5,405,137 A | 4/1995 | Vincent et al. | |
| 5,407,202 A | 4/1995 | Igarashi | |
| RE34,925 E | 5/1995 | McKeighen | |
| 5,417,419 A | 5/1995 | Anderson et al. | |
| 5,417,559 A | 5/1995 | Schmidt | |
| 5,423,535 A | 6/1995 | Shaw et al. | |
| 5,429,357 A | 7/1995 | Kobayashi | |
| 5,431,396 A | 7/1995 | Shieh | |
| 5,433,440 A | 7/1995 | Lin | |
| 5,447,307 A | 9/1995 | Antonious | |
| 5,447,309 A | 9/1995 | Vincent | |
| 5,451,056 A | 9/1995 | Manning | |
| 5,460,376 A | 10/1995 | Schmidt et al. | |
| 5,467,983 A | 11/1995 | Chen | |
| 5,470,069 A | 11/1995 | Schmidt et al. | |
| 5,474,296 A | 12/1995 | Schmidt et al. | |
| 5,482,279 A | 1/1996 | Antonious | |
| 5,497,993 A | 3/1996 | Shan | |
| 5,505,453 A | 4/1996 | Mack | |
| 5,522,593 A | 6/1996 | Kobayashi et al. | |
| 5,524,331 A | 6/1996 | Pond | |
| 5,533,729 A | 7/1996 | Leu | |
| 5,536,006 A | 7/1996 | Shieh | |
| 5,547,630 A | 8/1996 | Schmidt | |
| 5,549,297 A | 8/1996 | Mahaffey | |
| 5,564,994 A | 10/1996 | Chang | |
| 5,584,770 A | 12/1996 | Jensen | |
| 5,595,552 A | 1/1997 | Wright et al. | |
| 5,611,741 A | 3/1997 | Schmidt et al. | |
| 5,611,742 A | 3/1997 | Kobayashi | |
| D379,393 S | 5/1997 | Kubica et al. | |
| 5,626,530 A | 5/1997 | Schmidt et al. | |
| 5,643,104 A | 7/1997 | Antonious | |
| 5,643,108 A | 7/1997 | Cheng | |
| 5,643,110 A | 7/1997 | Igarashi | |
| 5,649,872 A | 7/1997 | Antonious | |
| 5,651,409 A | 7/1997 | Sheehan | |
| 5,655,976 A | 8/1997 | Rife | |
| 5,669,827 A | 9/1997 | Nagamoto | |
| 5,669,829 A | 9/1997 | Lin | |
| 5,674,132 A | 10/1997 | Fisher | |
| D387,113 S | 12/1997 | Burrows | |
| 5,695,411 A | 12/1997 | Wright et al. | |
| 5,709,614 A | 1/1998 | Horiba | |
| 5,709,615 A | 1/1998 | Liang | |
| 5,711,722 A | 1/1998 | Miyajima et al. | |
| 5,716,292 A | 2/1998 | Huang | |
| 5,718,641 A | 2/1998 | Lin | |
| 5,720,673 A | 2/1998 | Anderson | |
| 5,743,813 A | 4/1998 | Chen et al. | |
| 5,753,170 A | 5/1998 | Muang | |
| 5,755,624 A | 5/1998 | Helmstetter | |
| 5,755,627 A | 5/1998 | Yamazaki et al. | |
| 5,762,567 A | 6/1998 | Antonious | |
| 5,766,092 A | 6/1998 | Mimeur et al. | |
| 5,766,094 A | 6/1998 | Mahaffey et al. | |
| 5,766,095 A | 6/1998 | Antonious | |
| 5,776,011 A | 7/1998 | Su et al. | |
| 5,807,190 A | 9/1998 | Krumme et al. | |
| 5,827,132 A | 10/1998 | Bamber | |
| RE35,955 E | 11/1998 | Lu | |
| D401,652 S | 11/1998 | Burrows | |
| 5,830,084 A | 11/1998 | Kosmatka | |
| 5,839,975 A | 11/1998 | Lundberg | |
| 5,842,934 A | 12/1998 | Ezaki et al. | |
| 5,851,159 A | 12/1998 | Burrows | |
| 5,863,261 A | 1/1999 | Eggiman | |
| 5,873,791 A | 2/1999 | Allen | |
| 5,873,795 A | 2/1999 | Wozny et al. | |
| D406,294 S | 3/1999 | Burrows | |
| 5,888,148 A | 3/1999 | Allen | |

| | | | | | | |
|---|---|---|---|---|---|---|
| 5,890,973 | A | 4/1999 | Gamble | JP | 02130519 | 5/1990 |
| D411,272 | S | 6/1999 | Burrows | JP | 4020357 | 1/1992 |
| 5,908,357 | A | 6/1999 | Hsieh | JP | 4327864 | 11/1992 |
| 5,921,872 | A | 7/1999 | Kobayashi | JP | 5212526 | 8/1993 |
| 5,931,746 | A | 8/1999 | Soong | JP | 05237207 | 9/1993 |
| 5,935,019 | A | 8/1999 | Yamamoto | JP | 6007487 | 1/1994 |
| 5,938,541 | A | 8/1999 | Allen et al. | JP | 06031016 | 2/1994 |
| 5,941,782 | A | 8/1999 | Cook | JP | 6114126 | 4/1994 |
| 5,944,619 | A | 8/1999 | Cameron | JP | 6126002 | 5/1994 |
| 5,954,596 | A | 9/1999 | Noble et al. | JP | 6154367 | 6/1994 |
| D415,807 | S | 10/1999 | Werner et al. | JP | 6182005 | 7/1994 |
| 5,961,394 | A | 10/1999 | Minabe | JP | 6269518 | 9/1994 |
| 5,967,905 | A | 10/1999 | Nakahara et al. | JP | 8168541 | 7/1996 |
| 5,971,868 | A | 10/1999 | Kosmatka | JP | 8243194 | 9/1996 |
| 5,993,329 | A | 11/1999 | Shich | JP | 8280853 | 10/1996 |
| 6,007,432 | A | 12/1999 | Kosmatka | JP | 8280854 | 10/1996 |
| 6,027,416 | A | 2/2000 | Schmidt et al. | JP | 8294550 | 11/1996 |
| 6,139,445 | A | 10/2000 | Werner et al. | JP | 9028842 | 2/1997 |
| 6,152,833 | A | 11/2000 | Werner et al. | JP | 9047531 | 2/1997 |
| 6,248,025 | B1 | 6/2001 | Murphy | JP | 9154985 | 6/1997 |
| 6,319,150 | B1 | 11/2001 | Werner et al. | JP | 9168613 | 6/1997 |
| 6,338,683 | B1 | 1/2002 | Kosmatka | JP | 9192270 | 7/1997 |
| 6,354,962 | B1 | 3/2002 | Galloway | JP | 9192273 | 7/1997 |
| 6,368,234 | B1 | 4/2002 | Galloway | JP | 9239074 | 9/1997 |
| 6,381,828 | B1 | 5/2002 | Boyce | JP | 9239075 | 9/1997 |
| 6,390,933 | B1 | 5/2002 | Galloway | JP | 9248353 | 9/1997 |
| 6,398,666 | B1 | 6/2002 | Evans et al. | JP | 2717759 | 11/1997 |
| 6,435,982 | B1 | 8/2002 | Galloway et al. | JP | 9294833 | 11/1997 |
| 6,605,007 | B1 | 8/2003 | Bissonnette et al. | JP | 9299519 | 11/1997 |
| 6,899,638 | B2 | 5/2005 | Iwata et al. | JP | 10024126 | 1/1998 |
| 7,029,403 | B2 * | 4/2006 | Rice et al. ............ 473/329 | JP | 10024128 | 1/1998 |
| 7,207,898 | B2 * | 4/2007 | Rice et al. ............ 473/329 | JP | 10085369 | 4/1998 |
| 7,261,643 | B2 * | 8/2007 | Rice et al. ............ 473/329 | JP | 10118227 | 5/1998 |
| 7,331,877 | B2 * | 2/2008 | Yamaguchi et al. ...... 473/329 | JP | 10137372 | 5/1998 |
| 7,704,162 | B2 * | 4/2010 | Rice et al. ............ 473/329 | JP | 10155943 | 6/1998 |
| | | | | JP | 10258142 | 9/1998 |
| | | | | JP | 10263121 | 10/1998 |
| | | | | JP | 10323410 | 12/1998 |
| | | | | JP | 10337347 | 12/1998 |

FOREIGN PATENT DOCUMENTS

| | | | |
|---|---|---|---|
| GB | 2268693 | A | 1/1994 |
| GB | 2331938 | A | 6/1999 |
| JP | 59207169 | | 11/1984 |
| JP | 61033682 | | 2/1986 |
| JP | 61162967 | | 7/1986 |
| JP | 61181477 | | 8/1986 |
| JP | 61185281 | | 8/1986 |
| JP | 61240977 | | 10/1986 |
| JP | 1244770 | | 9/1989 |

OTHER PUBLICATIONS

Golf Digest, Dec. 1981, p. 58-59.
"Variable Face Thickness Technology," Calloway Golf advertisement, undated.

* cited by examiner

METAL WOOD CLUB WITH IMPROVED HITTING FACE

CROSS-REFERENCE TO RELATED APPLICATION

The present application is a continuation of U.S. patent application Ser. No. 11/221,221 filed on Sep. 7, 2005, now U.S. Pat. No. 7,704,162 which was a continuation-in-part of Ser. No. 10/911,422, now U.S. Pat. No. 7,261,643 and Ser. No. 10/911,341, now U.S. Pat. No. 7,207,898, both of which were filed on Aug. 4, 2004, and both of which were continuations-in-part of Ser. No. 10/428,061, now U.S. Pat. No. 7,029,403 filed on May 1, 2003, which is a continuation-in-part of Ser. No. 09/551,771, filed Apr. 18, 2000, now U.S. Pat. No. 6,605,007, the disclosures of which are all incorporated herein by reference in their entireties.

FIELD OF THE INVENTION

The present invention relates to an improved golf club head. More particularly, the present invention relates to a golf club head with an improved striking face having the longest characteristic time shifted away from the geometric center of the hitting face.

BACKGROUND

The complexities of golf club design are well known. The specifications for each component of the club (i.e., the club head, shaft, grip, and subcomponents thereof) directly impact the performance of the club. Thus, by varying the design specifications, a golf club can be tailored to have specific performance characteristics.

The design of club heads has long been studied. Among the more prominent considerations in club head design are loft, lie, face angle, horizontal face bulge, vertical face roll, center of gravity, inertia, material selection, and overall head weight. While this basic set of criteria is generally the focus of golf club engineering, several other design aspects must also be addressed. The interior design of the club head may be tailored to achieve particular characteristics, such as the inclusion of hosel or shaft attachment means, perimeter weights on the club head, and fillers within hollow club heads.

Golf club heads must also be strong to withstand the repeated impacts that occur during collisions between the golf club and the golf ball. The loading that occurs during this transient event can create a peak force of over 2,000 lbs. Thus, a major challenge is designing the club face and body to resist permanent deformation or failure by material yield or fracture. Conventional hollow metal wood drivers made from titanium typically have a uniform face thickness exceeding 2.5 mm to ensure structural integrity of the club head.

Players generally seek a metal wood driver and golf ball combination that delivers maximum distance and landing accuracy. The distance a ball travels after impact is dictated by the magnitude and direction of the ball's translational velocity and the ball's rotational velocity or spin. Environmental conditions, including atmospheric pressure, humidity, temperature, and wind speed, further influence the ball's flight. However, these environmental effects are beyond the control of the golf equipment manufacturer. Golf ball landing accuracy is driven by a number of factors as well. Some of these factors are attributed to club head design, such as center of gravity and club face flexibility.

Generally, golf ball travel distance is a function of the total kinetic energy imparted to the ball during impact with the club head, neglecting environmental effects. During impact, kinetic energy is transferred from the club and stored as elastic strain energy in the club head and as viscoelastic strain energy in the ball. After impact, the stored energy in the ball and in the club is transformed back into kinetic energy in the form of translational and rotational velocity of the ball, as well as the club. Since the collision is not perfectly elastic, a portion of energy is dissipated in club head vibration and in viscoelastic relaxation of the ball. Viscoelastic relaxation is a material property of the polymeric materials used in all manufactured golf balls.

Viscoelastic relaxation of the ball is a parasitic energy source, which is dependent upon the rate of deformation. To minimize this effect, the rate of deformation should be reduced. This may be accomplished by allowing more club face deformation during impact. Since metallic deformation may be purely elastic, the strain energy stored in the club face is returned to the ball after impact thereby increasing the ball's outbound velocity after impact.

A variety of techniques may be utilized to vary the deformation of the club face, including uniform face thinning, thinned faces with ribbed stiffeners and varying thickness, among others. These designs should have sufficient structural integrity to withstand repeated impacts without permanently deforming the club face. In general, conventional club heads also exhibit wide variations in initial ball speed after impact, depending on the impact location on the face of the club.

The United States Golf Association (USGA), the governing body for the rules of golf in the United States, issues specifications for the performance of golf balls and clubs. One such USGA rule limits the duration of the contact between the golf ball and the geometrical center of a club face, called the "characteristic time", to less than 257 microseconds. To maximize golf ball travel distance, a golf club's spring-like effect should be maximized while remaining within these rules. Hence, there remains a need in the art for a club head that has a maximized performance while adhering to USGA contact duration rules at the geometric center of the hitting face.

SUMMARY OF THE INVENTION

One aspect of the invention is a golf club head having a hitting face that includes a central zone having a first flexural stiffness and an intermediate zone having a second flexural stiffness. The second flexural stiffness is lower than the first. Locations of longest characteristic time are offset from the geometric center of the hitting face.

Another aspect of the invention is a golf club head having a hitting face that includes an elliptical central zone having a varying thickness. A minor axis of the central zone is thinner than a major axis of the central zone. A point of longest characteristic time is offset from a geometric center of the hitting face.

Another aspect of the invention is a golf club head having a hitting face that includes a central zone having a flexural stiffness which varies along a horizontal axis of the hitting face. A point of longest characteristic time is offset from the geometric center of the hitting face.

Yet another aspect of the invention is a golf club head having means for shifting a point of longest characteristic time away from a geometric center of the hitting face.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

U.S. Pat. No. 6,605,007, which has been incorporated herein in its entirety, discloses an improved golf club that also produces a relatively large "sweet zone" or zone of substantially uniform high initial velocity or high coefficient of restitution (COR). Increases or decreases in COR correspond generally but not directly to increases and decreases in the spring-like effect and characteristic time of a golf club head.

Figure 1:
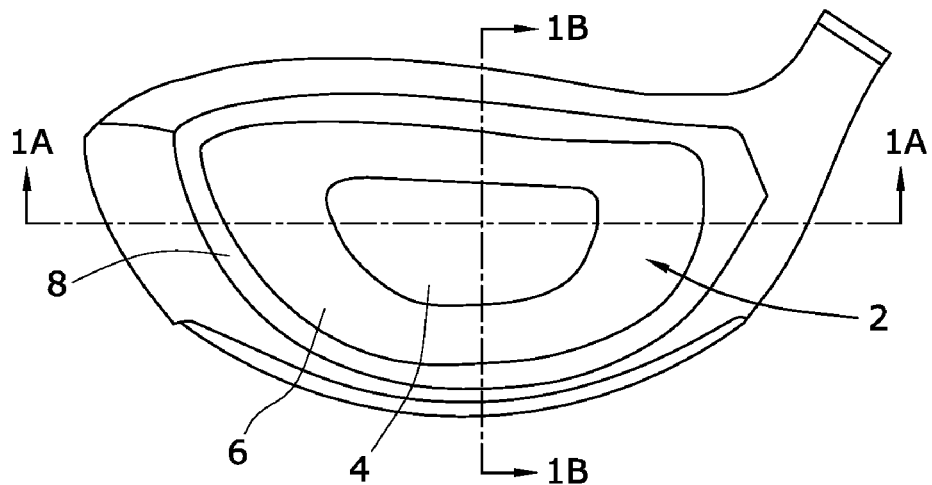
FIG. 1 is a front view of a striking face of the golf club head disclosed in the parent '422 and '321 applications.
Figure 1A:
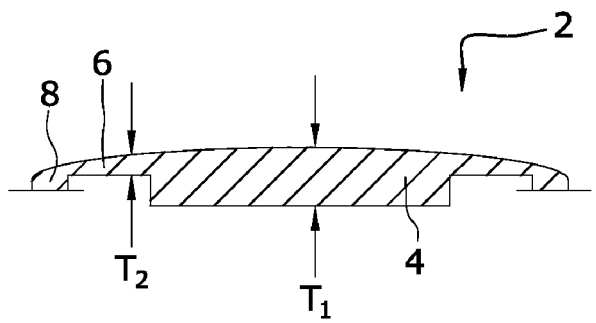
FIGS. 1A and 1B are cross-sectional views of the striking face of FIG. 1 taken along lines 1A-1A and 1B-1B, respectively.
Figure 1B:
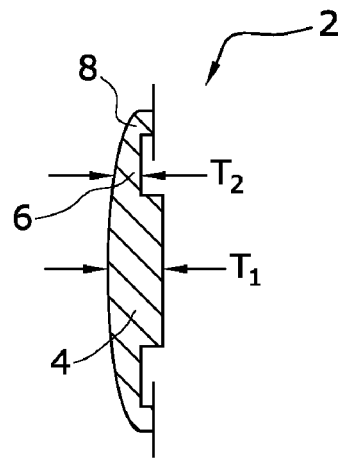

As shown in FIGS. 1, 1A and 1B, the accuracy of the club and the club's large zone of uniform high initial velocity are produced by a hitting face 2 of a club head 10. Hitting face 2 generally includes a central zone 4, a surrounding intermediate zone 6, and an optional perimeter zone 8. Preferably, the area of central zone 4 comprises less than about 15% of the total area of hitting face 2, and more preferably less than about 10% of the total area of hitting face 2.

Central zone 4 is comparatively rigid and intermediate zone 6 is relatively flexible so that upon ball impact, intermediate zone 6 of face 2 deforms, i.e., provides a desirable spring-like effect, to provide high ball velocity, while central zone 4 is substantially undeformed so that the ball flies on-target. Thus, upon ball impact the deformation of intermediate zone 6 allows central zone 4 to move into and out of club head 10 as a unit. Surrounding intermediate zone 6 may be located adjacent to central zone 4, and optional perimeter zone 8 may be located adjacent to intermediate zone 6. Since central zone 4, which incorporates the geometric center, deforms less than intermediate zone 6, the characteristic time is generally lower in central zone 4 than in intermediate zone 6.

The above is accomplished by providing central zone 4 with a first flexural stiffness and intermediate zone 6 with a second flexural stiffness. Flexural stiffness (FS) is defined as each portion's average elastic modulus (E) times each portion's average thickness (t) cubed or ($FS=Et^3$). The calculation of averages of modulus and thickness is fully disclosed in the parent application and in the '007 patent, which have already been incorporated by reference in their entireties. The determination of FS when the thickness varies or when the material is anisotropic is also fully discussed in the parent patent application and in the '007 patent.

Since the flexural stiffness is a function of material and thickness, the following techniques can be used to achieve the substantial difference between the flexural stiffness of central zone 4 and intermediate zone 6: 1) different materials can be used for each portion, 2) different thicknesses can be used for each portion, or 3) a combination of different materials and thickness can be used for each portion. For example, in a preferred embodiment, the thickness of central zone 4 is greater than the thickness of intermediate zone 6 and the material for both portions is the same. Central zone 4 may have a uniform thickness, or the thickness may vary.

In club head 10, the above flexural stiffness relationships can be achieved by selecting a certain material with a particular elastic modulus and varying the thickness of the zones. In another embodiment, the flexural stiffness relationships can be achieved by varying the materials of the zones with respect to one another so that the zones have different elastic moduli and the thickness is changed accordingly. Thus, the thickness of the zones can be the same or different depending on the elastic modulus of the material of each zone. The required flexural stiffness ratio may also be obtained through the use of structural ribs, reinforcing plates, and thickness parameters. The '061 application and the '007 patent describe in detail a preferred ranges of ratios of flexural stiffness between central zone 4 and intermediate zone 6.

Due to hitting face 2 having stiffened central zones 4, as compared with intermediate zone 6 and/or optional perimeter zone 8, the location of longest characteristic time is not at the geometric center of hitting face 2. The performance of hitting face 2 is optimized over the entire area of face 2 instead of at the geometric center of hitting face 2. As USGA club conformance standards using the pendulum test method described herein are based upon the characteristic time, i.e., the duration of contact between a probe and the club hitting face, only at the geometric center of the hitting face, hitting face 2 may have locations having longer characteristic times while staying within the USGA rules. This shifting of the location of longest characteristic time is found on hitting face structures that raise the stiffness of central zone 4 or, similarly, decreases the stiffness of intermediate zone 6. Several examples of such hitting face configurations are discussed below and further described or disclosed in the parent '422, '341, and '061 applications, as well as the parent '007 patent.

Figure 1C:
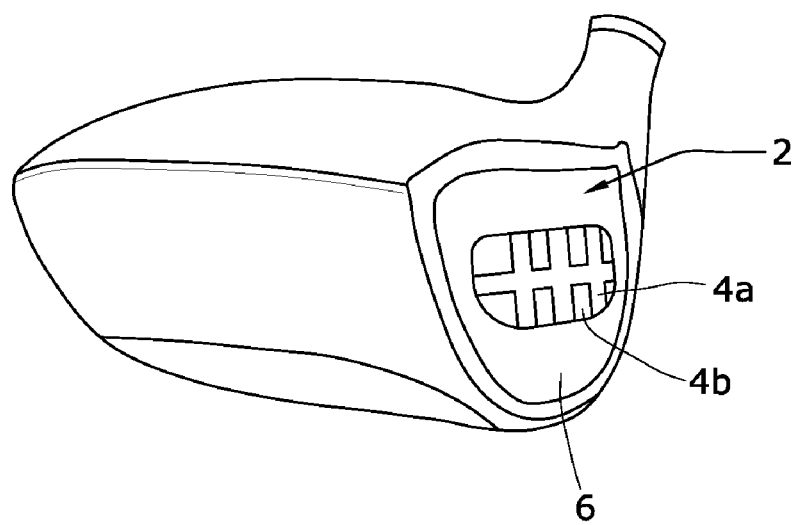
FIG. 1C is an alternate embodiment from the priority patent.

One example of a hitting face 2 configuration that shifts the location of longest characteristic time away from the geometric center of hitting face 2 is when two or more different homogeneous materials are be used to form hitting face 2, as discussed in the '007 patent. In one embodiment, discussed for the purposes of example only, central zone 4 may be of generally uniform thickness and made from a stainless steel having a Young's Modulus of $30.0 \times 10^6$ lbs/in². The adjacent intermediate zone 6 has a continuously tapering thickness from the face perimeter toward central zone 4. The thickness of intermediate zone 6 is defined in this example to change linearly. Intermediate zone 6 is made from a titanium alloy having a Young's Modulus of $16.5 \times 10^6$ lbs/in². Alternatively, as shown in FIG. 1C, which corresponds to FIG. 10 from the '007 patent, central zone 4 may include ribs 4a made of stainless steel having a Young's Modulus of $30.0 \times 10^6$ lbs/in$^2$ with a titanium alloy having a Young's Modulus of $16.5 \times 10^6$ lbs/in$^2$ in the interstitial spaces 4b. Intermediate zone 6 is made from the same titanium alloy. The flexural stiffness ratio between central zone 4 and intermediate zone 6 is calculated in detail in the '007 patent. As will be recognized by those in the art, the present invention contemplates the use of many different materials and thickness profile combinations in addition to the specific examples discussed herein.

Optional perimeter zone 8 can increase or decrease in flexural stiffness as compared with intermediate zone 6 or even remain the same in respect of flexural stiffness. Optional perimeter zone preferably decreases in thickness compared to intermediate zone 6 to decrease the flexural stiffness of perimeter zone 8 relative to intermediate zone 6. Alternatively, optional perimeter zone 8 may decrease in flexural stiffness compared to intermediate zone 6 by forming perimeter zone 8 out of a different material than that of intermediate zone 6. For example, perimeter zone 8 may be made of the same material as central zone 4. Alternatively, perimeter zone 8 may be made of an entirely different material than that of central zone 4 or intermediate zone 6. Perimeter zone 8 would then be attached to intermediate zone 6 by any method known in the art, such as by welding.

Figure 2:
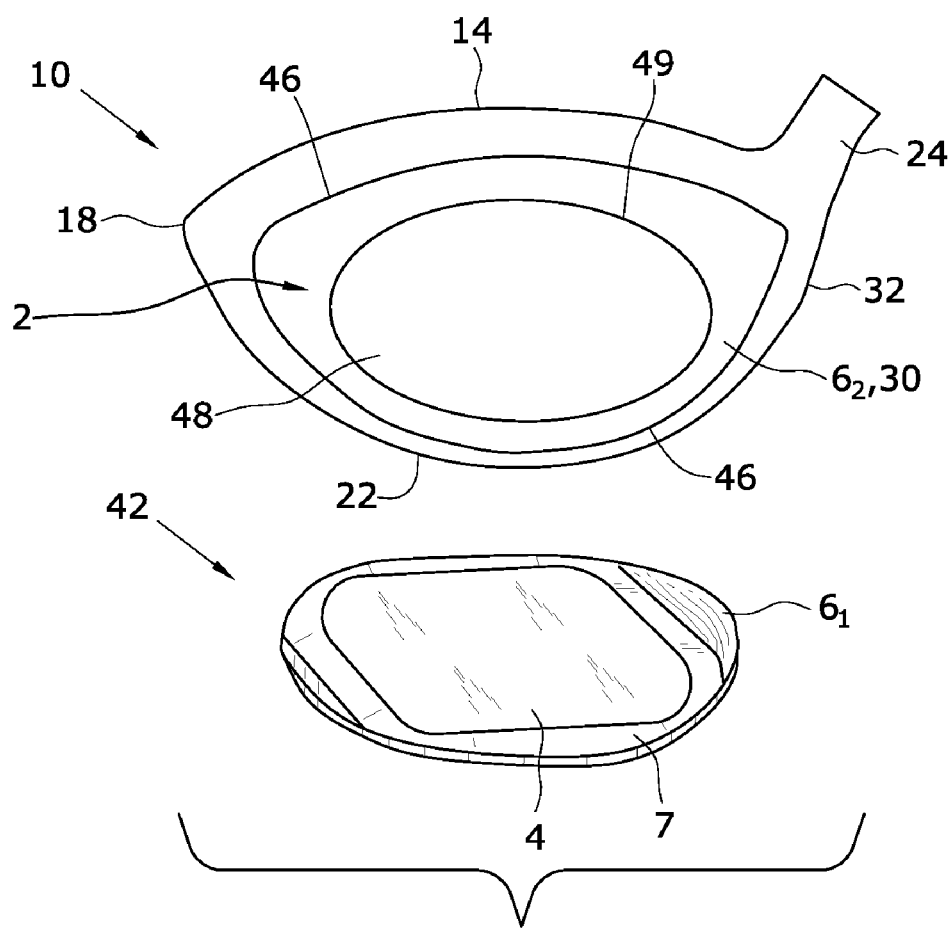
FIG. 2 is a front, exploded view of an alternate embodiment disclosed in the parent '422 and '321 applications.
Figure 8:
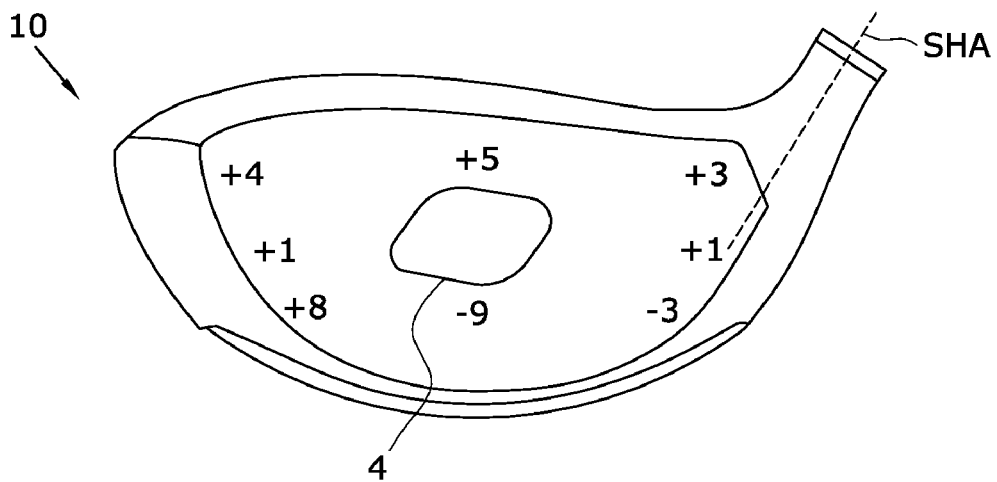
FIG. 8 is a front view of a third inventive club head showing the deviation of characteristic time from the geometric center of the club face.

Referring to FIG. 2, which corresponds to FIG. 8 from the parent '061 application, another example of a configuration of hitting face 2 where the location of longest characteristic time is shifted away from the geometric center of hitting face 2 is shown. Hollow metal wood club head 10 has a hitting face 2 which includes a face insert 42 and face support 30. Face insert 42 fits into a similarly shaped opening in face support 30 and is affixed therewithin by any method known in the art, such as by welding. In this embodiment, hitting face 2 is delineated from crown 14, toe 18, sole 22 and heel 32 by parting line 46.

Central zone 4 is preferably disposed on the inner-cavity-facing surface of face insert 42, and, as shown, preferably has a generally elliptical shape. As defined in the parent case, the term "ellipse" or "elliptical" refers to non-circular shapes that have discernable major axis and minor axis, and include, but are not limited to, any quadrilateral shapes, geometrical ellipses, quadrilateral shapes with one or more rounded corner(s) and unsymmetrical elliptical shapes. The "major axis" is defined as the axis coinciding with the longest length that can be drawn through the non-circular shapes without intersecting the perimeter of the shapes at more than two locations, i.e., at the start and end points of said length. The "minor axis" is orthogonal to the major axis at or near its midpoint. As used herein, the term "concentric" refers to shapes that substantially encircle or surround other shapes.

One embodiment having an elliptical central zone 4 is disclosed in the parent '061 application. In another embodiment, central zone 4 preferably includes a varying thickness profile where the minor axis of central zone 4 is thinner than the major axis of central zone 4. Central zone 4 is preferably positioned within face support 30 such that the major axis of central zone 4 is aligned in the direction of the low toe to high heel, so that a sweet spot, can be established in the direction of high toe to low heel. This sweet spot advantageously coincides with the typical impact patterns created by golfers. As central zone 4 is stiffer than the surrounding zones, the point of longest characteristic time is shifted away from a geometric center of hitting face 2, with the geometric center being preferably located within central zone 4.

Intermediate zone 6, designated as $6_1$ and $6_2$, can be disposed partially on face insert 42 and partially on face support 30. A transition zone 7 having variable thickness is disposed between central zone 4 and intermediate zone 6. Preferably, the thickness of transition zone 7 matches the thickness of central zone 4 where transition zone 7 and central zone 4 meet. Transition zone 7 then tapers to the reduced thickness of intermediate zone 6. This tapering of transition zone 7 reduces any local stress-strain caused by impacts with golf balls due to abrupt changes in thickness.

Preferably, face insert 42 is made by milling or stamping and forming. In the manufacturing process, a malleable metal suitable for use as a hitting face, such as titanium, titanium alloy, carbon steel, stainless steel, beryllium copper, and other formable metals, is heated and then hammered into the desired shape of the face cup. Examples of some appropriate metals include but are not limited to titanium 6-4 alloy, titanium 15-3-3-3 alloy, titanium 20-4-1 alloy, and DAT 55 and DAT 55G, titanium alloys available from Dido Steel of Tokyo, Japan.

Figure 3:
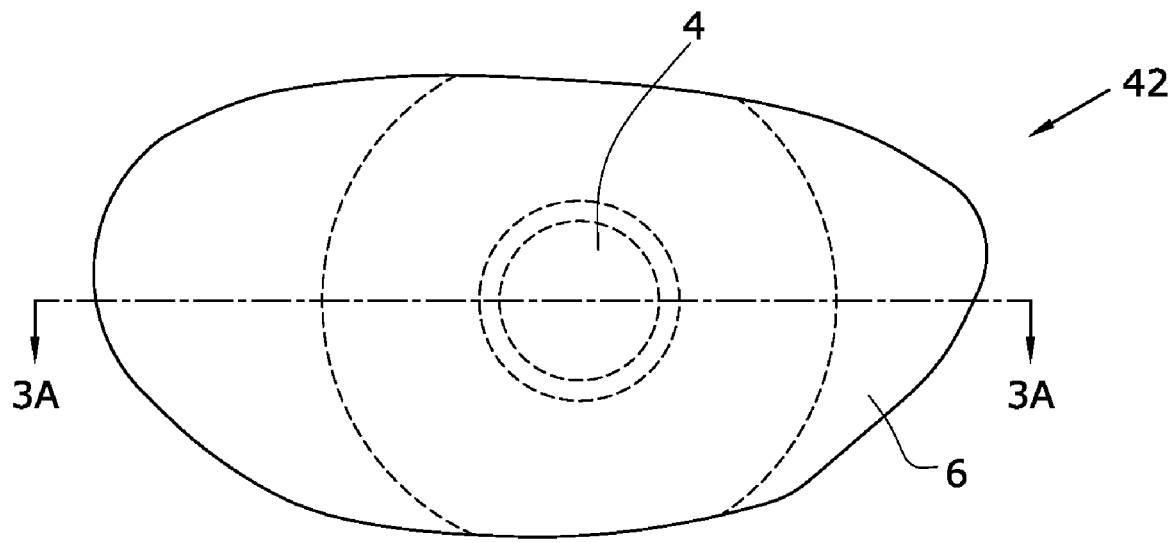
FIG. 3 is a front plan view of an embodiment of a hitting face disclosed in the parent '422 and '321 applications.
Figure 3A:
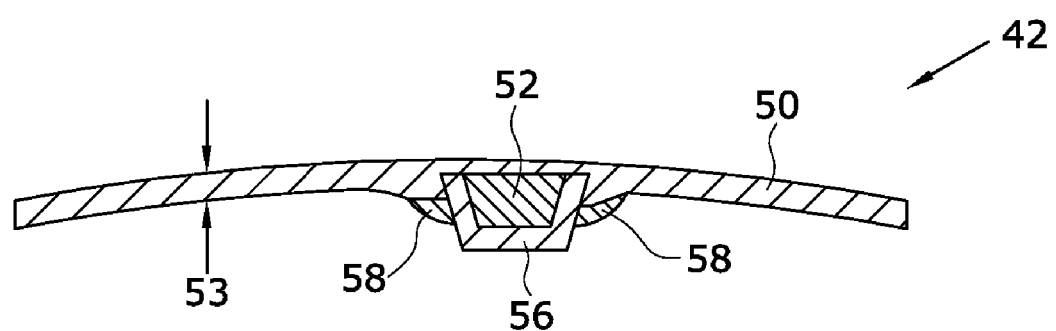
FIG. 3A is a cross-sectional view of the hitting face of FIG. 3 taken along line 3A-3A thereof.

Referring to FIG. 3, which corresponds to FIG. 3 from the parent '422 application, an alternate embodiment of hitting face insert 42 is shown. In this embodiment, the flexural stiffness of central zone 4 is higher than the flexural stiffness of intermediate area 6 due to a dense insert 52 made of a material of greater density than that of the material forming the remainder of face insert 42. As the flexural stiffness of central zone 4 is higher than that of intermediate area 6, the characteristic time for central zone 4 is lower than that of intermediate area 6. In other words, dense insert 52 causes the location of the longest characteristic time to be shifted away from the geometric center of hitting face insert 42, with the geometric center being preferably located within central zone 4. A cross-sectional view of a preferred embodiment of the present invention is shown in FIG. 3A, wherein face insert 42 includes a plate-like face 50 and an insert 52.

Plate-like face 50 is preferably elliptical in shape with a slightly curved profile, although any shape may be used, such as polygonal, circular or irregular. Plate-like face 50 may be made of any material discussed herein that is suitable for forming hitting face 2, such as titanium, titanium alloy, carbon steel, stainless steel, beryllium copper. The more preferred metal is titanium 6-4 alloy, as described above. The size of plate-like face 50 depends upon the overall size of golf club head 10. However, in a preferred embodiment, plate-like face 50 measures between 80 and 100 mm along the long axis of the ellipse and between 35 and 60 mm along the short axis of the ellipse. More preferably, plate-like face 50 measures 90 mm along the long axis of the ellipse and 50 mm along the short axis. Plate-like face 50 may be of uniform or non-uniform thickness 53. In one embodiment, thickness 53 ranges from 2-5 mm. Preferably, thickness 53 is 2.7 mm gradually tapering to a maximum thickness of 4.5 mm.

Dense insert 52, as shown, is preferably a conical frusta that is relatively small in cross-sectional surface area compared to plate-like face 50. Dense insert 52 may take on any shape that is convenient for manufacturing, for example a cylinder or a circular, elliptical or quadrilateral disk. Dense insert 52 is made of a material of greater density than that of plate-like face 50, preferably tungsten or stainless steel, although any material of greater density than plate-like face 50 is appropriate for use in the present invention, including copper, nickel, and bronze. Dense insert 52 may be milled, stamped from sheet metal, forged, die cut, cast, or made using any technique known in the art.

Dense insert 52 is preferably small compared to the size of plate-like face 50. In one embodiment, dense insert 52 is approximately 10 mm in diameter at its widest point and approximately 7 mm in height. As such, dense insert 52 protrudes from surface 55 of plate-like face 50, as dense insert 52 is of a greater height than the depth of cavity 51. The size of dense insert 52 may be varied so as to control the effective size of central zone 4.

Dense insert 52 may be directly or indirectly affixed to plate-like face 50. In one embodiment, dense insert 52 is contained within a cap 56 made of the same material as that used to make plate-like face 50 so that cap 56 may be readily welded to plate-like face 50. Dense insert 52 may be affixed to an interior surface of cap 56, adhered to at least one interior surface of cap 56, or simply rest within cap 56. As shown, cap 56 is a conical frusta having an interior cavity shaped so that dense insert 52 fits tightly within cap 56. Cap 56 may be made using any method known in the art, such as casting, stamping or forging.

As such, dense insert 52 is indirectly fixedly attached to plate-like face 50, in that dense insert 52 is contained within cap 56 which is joined to plate-like face 50 by a weld bead 58 so that dense insert 52 is not dislodged from its position during the repeated impacts of hitting face 2 with golf balls. Alternately, at least a portion of the combination of dense insert 52 and cap 56 may be secured within cavity 51 using an adhesive, for example hot melt adhesives, epoxy adhesives, polyurethane adhesives, sealants, thermoset adhesives, UV curing adhesives, silicon adhesives, acrylic and cyanoacrylic adhesives.

Figure 4:
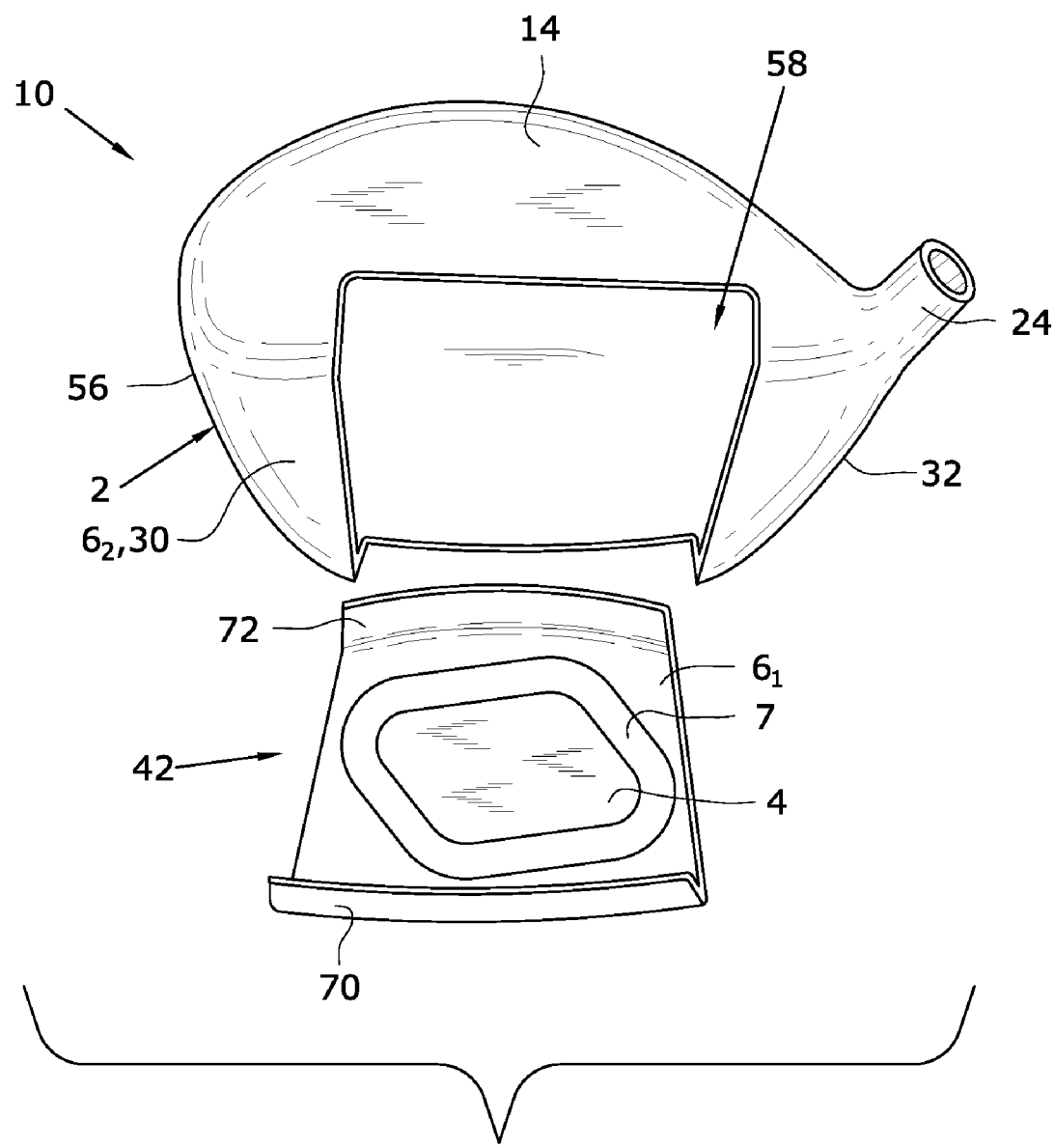
FIG. 4 is a front exploded view of an alternate embodiment of a club head disclosed in the '422 and '321 applications.
Figure 9:
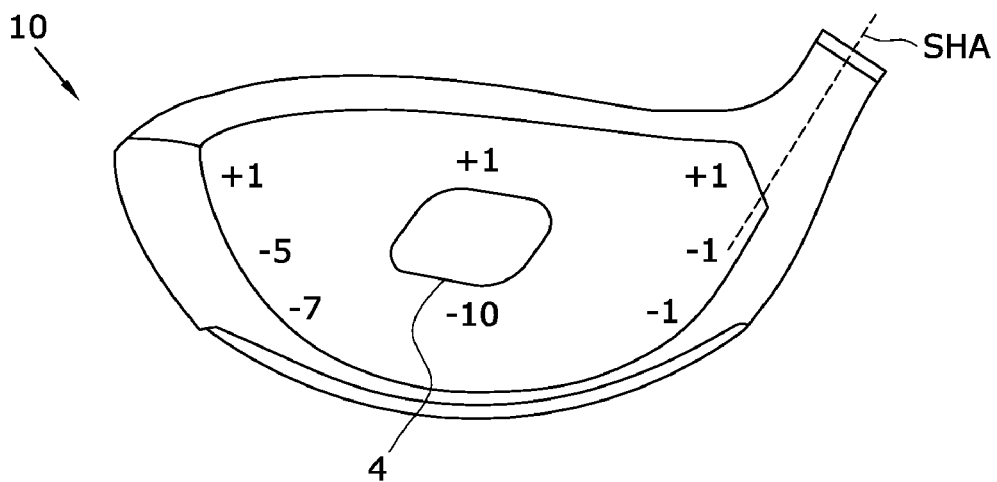
FIG. 9 is a front view of a fourth inventive club head showing the statistical frequency of hits at various locations on the club face as well as the deviation of characteristic time from the geometric center of the club face.

Referring to FIG. 4, which corresponds to FIG. 9 from the parent '422 application, yet another embodiment of a hitting face 2 where the location of longest characteristic time is shifted away from the geometric center thereof is shown. Hitting face 2 includes a face insert 42 that comprises a central zone 4, a transition zone 7, a portion of an intermediate zone 6, a partial crown portion 54 and a partial sole portion 56. Club head 10 correspondingly defines a cavity 58 sized and dimensioned to receive face insert 42. Face insert 42 is preferably welded to club head 10. Face insert 42 together with face support 30 forms hitting face 2. Similar to the embodiment illustrated in FIG. 2, intermediate zone 6, designated as $6_1$ and $6_2$, can be disposed partially on face insert 42 and partially on face support 30.

Face insert 42 is preferably made from the same material as the rest of club head 10, such as titanium, a titanium alloy, steel, or any other material suitable for use as a club head. Face insert 42 is preferably the same thickness as the rest of club head 10, although face insert 42 may be made thicker or thinner in order to affect the flexural stiffness thereof.

The material properties of face insert 42 can also be affected by the method chosen to form face insert 42. For example, face insert 42 is preferably stamped or milled from sheet metal after the metal has been cold rolled or cold worked in order to align the crystal grains of the metal. Stamping metal in this fashion produces a stronger hitting face than other manufacturing techniques. Further, face insert 42 is then positioned within hitting face 2 so that the grain flow pattern of face insert 42 runs in a sole-to-crown direction. Alternatively, the grain flow pattern of face insert 42 may run in a heel-to-toe direction or in a diagonal direction. Other methods known in the art may also be used to manufacture face insert 42, such as forging and casting.

Hitting face 2 in any of the embodiments described above is preferably milled or stamped and milled. The body of club 10 is preferably cast. The inner cavity of club head 10 may be empty, or alternatively may be filled with foam or other low specific gravity material. It is preferred that the inner cavity has a volume greater than 250 cubic centimeters, and more preferably greater than 275 cubic centimeters, and most preferably 350 cubic centimeters or more. Preferably, the mass of the inventive club head is greater than 150 grams but less than 220 grams. Further part and manufacturing details and additional test results regarding the COR values of inventive club heads are discussed in detail in the parent cases.

Figure 5:
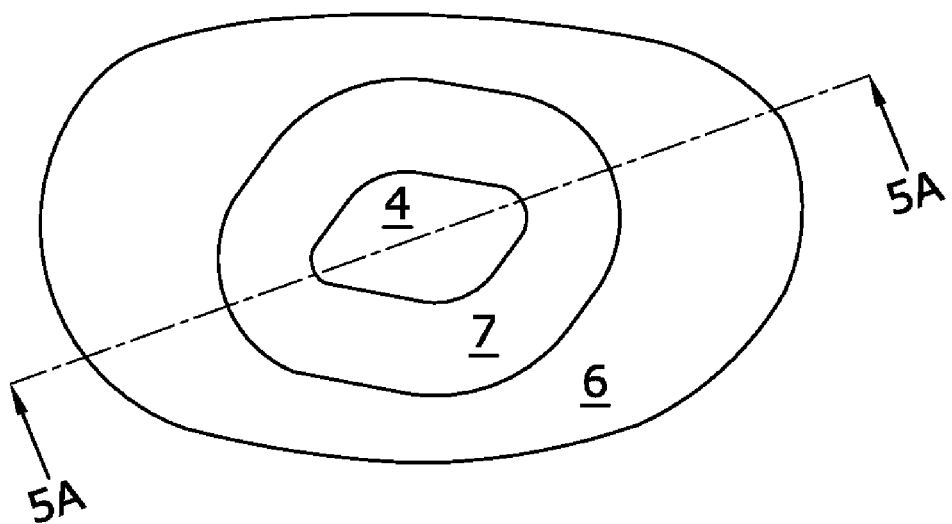
FIG. 5 is a schematic view of an embodiment of a club head according to the present invention showing zones of varying flexural thickness.
Figure 5A:
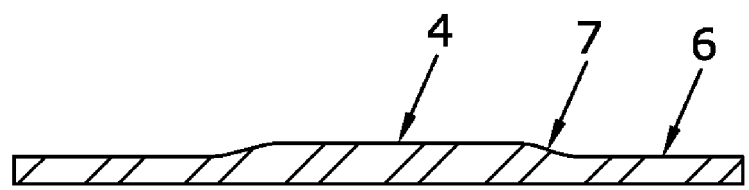
FIG. 5A is a cross-sectional view of the club head of FIG. 5 taken along line 5A-5A thereof.

Table 1 shows how the characteristic time varies across the hitting faces of various inventive clubs. Each inventive club is a hollow metal wood club head made generally in accordance with the embodiment shown in FIG. 4. FIG. 5 shows a schematic view of a hitting face for use in any of the inventive clubs, with a central zone 4 in the shape of a rhombus surrounded by a thinner intermediate zone 6 with a transitional zone 7 having a tapered thickness to join central zone 4 and intermediate zone 6 in a smooth radius. This smooth transition of thicknesses is shown more clearly in FIG. 5A, which shows a cross-sectional view of hitting face.

Each inventive club has a slightly different varying thickness profile. Central zone 4 of Inventive Club #1 has a thickness of 0.43 cm. Intermediate zone 6 has a thickness of 0.255 cm, and the transitional zone 7 has a tapered radius thickness profile that ranges from 0.255 cm adjacent to intermediate zone 6 to 0.43 cm adjacent to central zone 4. The hitting face insert of Club #1 was made by stamping. The rhombus pad has an area of approximately 2.1 cm$^2$.

Inventive Club #2 is similar to Club #1, including a hitting face insert 42 having a central zone 4 having a rhombus shape approximately the same size as the rhombus pad of Club #1, approximately 2.1 cm$^2$. However, the thickness of the rhombus is 0.34 cm, with an intermediate zone 6 of 0.26 cm.

Inventive Club #3 is the same as Club #2, except that the size of the rhombus pad for Club #3 is one-quarter of the size (in terms of surface area) of the rhombus pad for Club #2, or about 0.52 cm$^2$. However, the thicknesses of the different zones in Club #3 are the same as those for Club #2. Similarly, Inventive Club #4 is the same as Club #2, except that the size of the rhombus pad for Club #4 is one-half the size (in terms of surface area) of the rhombus pad for Club #2, or about 1.03 cm$^2$. The thicknesses of the different zones in Club #4 are the same as those for Club #2 and Club #3.

All inventive clubs were tested using the pendulum test, which is the standard test for club face flexibility or trampoline effect under current USGA and international rules. This test entails impacting a specific spot on a golf club hitting face several times using a small steel pendulum. The characteristic time, the length of duration of contact between the club head and the pendulum, is measured in microseconds (µs). Generally, the longer the characteristic time, the greater the flexibility of the golf club hitting face. In accordance with USGA rules, the geometric center of the golf club hitting face is tested. The maximum characteristic time allowed at the geometric center (labeled "Center" on Table 1) by current USGA rules is 239 µs+18 µs. However, the inventive clubs were tested at various spots on the hitting face to show how the characteristic time varies over the hitting face. Additionally, Table 2 shows the deviation of characteristic times from the geometric center of the clubs.

TABLE 1

Characteristic Times for Inventive Clubs #1-4
Characteristic Time (μs)

| Head | Hi Toe | Hi Center | Hi Heel | Toe | Center | Heel | Low Toe | Low Center | Low Heel |
|---|---|---|---|---|---|---|---|---|---|
| Inventive Club #1 | 239 | 221 | 234 | 230 | 219 | 227 | 216 | 217 | 219 |
| Inventive Club #2 | 257 | 258 | 261 | 255 | 259 | 256 | 251 | 250 | 257 |
| Inventive Club #3 | 268 | 269 | 267 | 265 | 264 | 265 | 256 | 255 | 261 |
| Inventive Club #4 | 264 | 264 | 264 | 258 | 263 | 262 | 256 | 253 | 262 |

TABLE 2

Deviation of Characteristic Time at Various Locations from Center
Characteristic Time (μs)

| Head | Hi Toe | Hi Center | Hi Heel | Toe | Center | Heel | Low Toe | Low Center | Low Heel |
|---|---|---|---|---|---|---|---|---|---|
| Inventive Club #1 | +20 | +2 | +15 | +11 | 0 | +8 | −3 | −2 | 0 |
| Inventive Club #2 | −2 | −1 | +2 | −4 | 0 | −3 | −8 | −9 | −2 |
| Inventive Club #3 | +4 | +5 | +3 | +1 | 0 | +1 | −8 | −9 | −3 |
| Inventive Club #4 | +1 | +1 | +1 | −5 | 0 | −1 | −7 | −10 | −1 |

As can be seen in Tables 1 and 2, the characteristic time at the geometric center of the hitting face does not have the longest characteristic time for any of the inventive clubs. This reduced characteristic time at the geometric center is due, in part, to the increased thickness of the hitting face at the geometric center compared to the transitional and/or intermediate zones of the hitting face. In other words, by stiffening the geometric center while making the rest of the hitting face more flexible, the perimeter of the hitting face is generally more flexible than the geometric center of the hitting face. By having a hitting face perimeter that is more flexible than the geometric center of the hitting face, it is possible to comply with the USGA rules for characteristic time at the geometric center while maximizing the flexibility of the hitting face by increasing overall face deflection efficiency.

Figure 6:
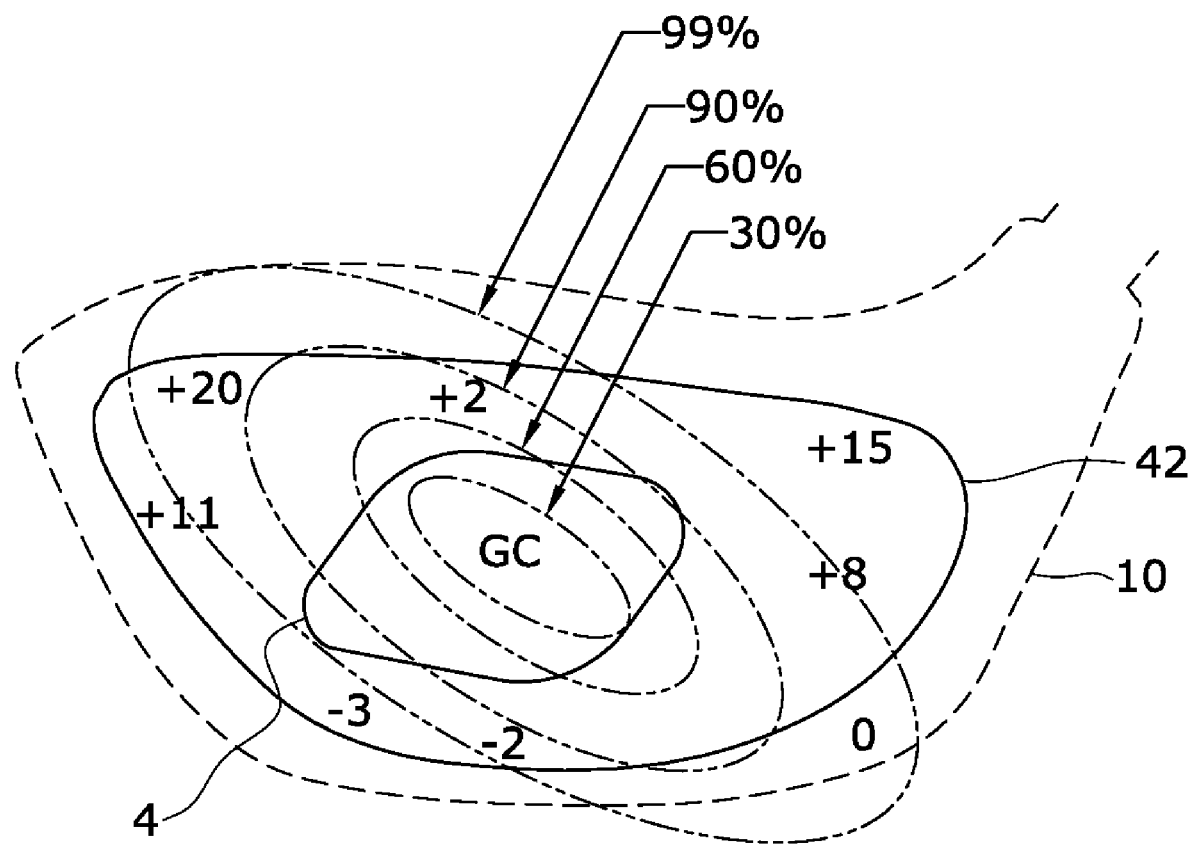
FIG. 6 is a schematic view of a first inventive club head showing the statistical frequency of hits at various locations on the club face as well as the deviation of characteristic time from the geometric center of the club face.

Further, as shown in FIG. 6, a golf club head 10 can be designed so that the location of longest characteristic time matches the most likely distribution of hits for an average golfer. As discussed in FRANK D. WERNER and RICHARD C. GRIEG, HOW GOLF CLUBS REALLY WORK AND HOW TO OPTIMIZE THEIR DESIGNS, pp. 18-20, Origin, Inc. (2000), players tend to hit the striking face of a golf ball in an elliptical upper toe-to-lower heel pattern. FIG. 6 shows the statistical distribution of striking points on the hitting face for a golfer having a handicap of 20. FIG. 6 shows the deviation of characteristic times for the various locations on the hitting face from the characteristic time at the geometric center for Club #1. Some of the longest characteristic times, e.g., high toe, toe, heel, are located within the elliptical patterns, thereby assisting high handicap players to strike the ball better. While many factors are considered when designing a club head, such as materials, manufacturing methods and overall face geometry, the use of zones having differing flexural stiffness in order to shift the location of longest characteristic time away from the geometric center provides additional design flexibility.

Figure 7:
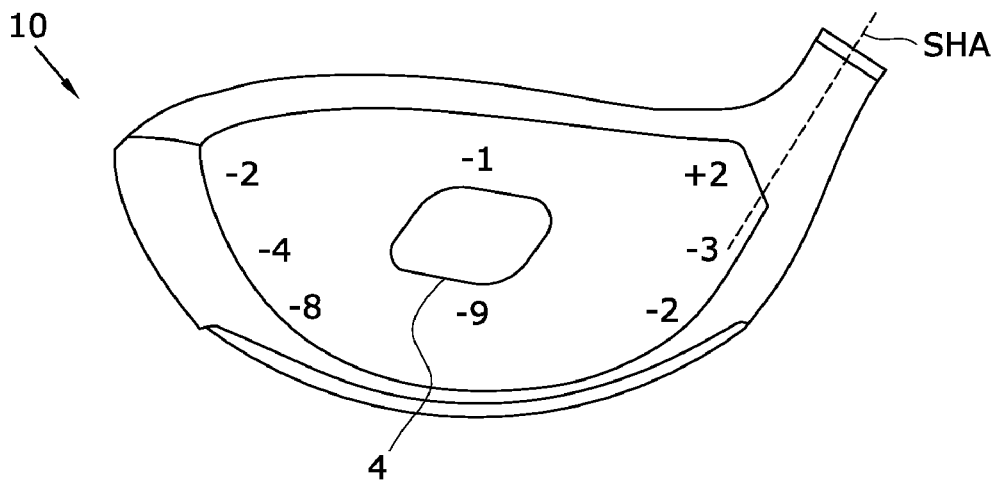
FIG. 7 is a front view of a second inventive club head showing the deviation of characteristic time from the geometric center of the club face.

Additionally, as shown in FIGS. 7-9, the size of central zone 4 has a significant impact on the characteristic time. For example, Club #2, which has the largest central zone 4, has the least deviation from the characteristic time at the geometric center of the hitting face. Furthermore, when the characteristic time does shift a large amount, such as in the low toe region, the effect is to reduce the characteristic time. A similar effect is seen in Club #4, which has a central zone 4 that is ¼ the size of central zone 4 in Club #2. However, in Club #3, which has a central zone 4 that is ½ the size of central zone 4 in Club #2, the characteristic time is optimized in the high toe region, which is also a location where, statistically, a player is more likely to hit the hitting face.

While various descriptions of the present invention are described above, it should be understood that the various features of each embodiment could be used alone or in any combination thereof. Therefore, this invention is not to be limited to only the specifically preferred embodiments depicted herein. Further, it should be understood that variations and modifications within the spirit and scope of the invention might occur to those skilled in the art to which the invention pertains. For example, any hitting face structure that increases stiffness at the geometric center as compared to the hitting face perimeter is appropriate, so the present invention is not limited to only those structures disclosed herein. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

The invention claimed is:

1. A golf club head comprising:
   a hitting face having,
      a central zone having a first flexural stiffness, and
      an intermediate zone concentric with the central zone,
   wherein the intermediate zone has a second flexural stiffness that is lower than the first flexural stiffness, and
   wherein a location of the longest characteristic time is offset from a geometric center of the hitting face; and
   wherein a projected area of the central zone is less than about 10% of a total projected area of the hitting face,
   wherein the projected area of the central zone and the projected area of the hitting face are calculated based on a two-dimensional frontal projection of the hitting face taken from a front view of the striking face.

2. The golf club head of claim 1, wherein the central zone contains a geometric center that approximately coincides with the geometric center of the hitting face.

3. The golf club head of claim 1, wherein said hitting face further comprising:
   a face support around a perimeter of the hitting face; and
   a face insert located within the center of the hitting face;
   wherein the intermediate zone is disposed partially on the face insert and partially on face support.

4. The golf club head of claim 3, wherein the intermediate zone is thinner than the central zone.

5. The golf club head of claim 3, wherein the intermediate zone has the same thickness as the central zone.

6. The golf club head of claim 5, wherein the intermediate zone comprises a first material and the central zone comprises a second material, and the first material is less dense than the second material.

7. The golf club head of claim 3, wherein the location of the longest characteristic time is offset from the geometric center toward the club head's toe.

8. The golf club head of claim 3, wherein the location of the longest characteristic time is offset from the geometric center toward the club head's crown.

9. The golf club head of claim 3, wherein the location of the longest characteristic time is offset from the geometric center toward the club head's heel.

10. A golf club head comprising:
    a hitting face having,
       a central zone having a first flexural stiffness; and
       an intermediate zone having a second flexural stiffness,
    wherein the intermediate zone is concentric with the central zone,
    wherein the second flexural stiffness is lower than the first flexural stiffness, and
    wherein a location of the longest characteristic time is offset from a geometric center of the hitting face;
    the hitting face further comprising,
       a face support provided around a perimeter of the hitting face; and
       a face insert located within the center of the hitting face;
          wherein the intermediate zone is disposed partially on the face insert and partially on the face support.

11. The golf club head of claim 10, wherein the central zone is positioned at the geometric center of the hitting face and has a generally elliptical shape with a major axis and a minor axis.

12. The golf club head of claim 11, wherein the geometric center of the central zone is the intersection between the major axis and the minor axis.

13. The golf club head of claim 12, wherein a projected area of the central zone is less than about 15% of a total projected area of the hitting face, and
    wherein the projected area of the central zone and the projected area of the hitting face are calculated based on a two-dimensional frontal projection of the hitting face taken from a front view of the striking face.

14. The golf club head of claim 10, wherein said major axis aligns substantially in the direction of high heel to low toe.

* * * * *